United States Patent [19]

Zagnoli

[11] Patent Number: 5,661,137
[45] Date of Patent: Aug. 26, 1997

[54] ANTACID PHARMACEUTICAL COMPOSITION IN THE FORM OF A SUSPENSION BASED ON SUCRALFATE GEL

[75] Inventor: Giorgio Zagnoli, Como, Italy

[73] Assignee: Laboratorio Italiano Biochimico Farmaceutico Lisapharma S.p.A., Erba, Italy

[21] Appl. No.: 591,647

[22] PCT Filed: Jul. 27, 1994

[86] PCT No.: PCT/EP94/02477

§ 371 Date: Jan. 29, 1996

§ 102(e) Date: Jan. 29, 1996

[87] PCT Pub. No.: WO95/03808

PCT Pub. Date: Feb. 9, 1995

[30] Foreign Application Priority Data

Jul. 30, 1993 [IT] Italy .................. MI93A1742

[51] Int. Cl.$^6$ .................. A61K 31/715; A61K 33/10; A61K 33/08
[52] U.S. Cl. .................. 514/53; 424/686; 424/687; 424/692
[58] Field of Search .................. 514/53; 424/686, 424/687, 692

[56] References Cited

U.S. PATENT DOCUMENTS

| 5,246,697 | 9/1993 | Conte et al. | 424/78.03 |
| 5,321,013 | 6/1994 | Zagnoli et al. | 514/53 |

FOREIGN PATENT DOCUMENTS

| 0245855 | 11/1987 | European Pat. Off. . |
| 0286978 | 10/1988 | European Pat. Off. . |
| 0331385 | 9/1989 | European Pat. Off. . |
| 0403048 | 12/1990 | European Pat. Off. . |
| 0437406 | 1/1991 | European Pat. Off. . |
| 0511703 | 11/1992 | European Pat. Off. . |
| 9311750 | 6/1993 | WIPO . |

OTHER PUBLICATIONS

"Avery's Drug Treatment", T.M. Speight Ed., pp. 742–743. 1987.
J.E.F. Reynolds–Martindale, "The Extra Pharmacopeia" 29th Edition, p. 1108, 707-m (1989).

*Primary Examiner*—Raymond Henley, III
*Attorney, Agent, or Firm*—Abelman, Frayne & Schwab

[57] ABSTRACT

Antiacid pharmaceutical compositions in the form of suspensions containing sucralphate gel as an active ingredient combined with suitable excipients and/or diluents.

4 Claims, 3 Drawing Sheets

ANTACID PHARMACEUTICAL COMPOSITION IN THE FORM OF A SUSPENSION BASED ON SUCRALFATE GEL

This application is a 371 of PCT/EP94/02477 filed Jul. 27, 1994.

FIELD OF THE INVENTION

The present invention relates to antacid pharmaceutical compositions in the form of suspensions containing sucralfate gel as an active ingredient combined with suitable excipients and/or diluents.

STATE OF THE ART

Sucralfate, i.e. the complex of sulphated sucrose and aluminium hydroxide, is an antiulcer drug. It exerts an inhibitory action against pepsin and, as more recently found, a cytoprotective action. In the solid state, sucralfate reacts with the acids of the stomach giving a tacky mucosa-adhesive substance, denominated paste. Said tacky substance is deemed essential to secure the antiulcer activity of sucralfate: it adheres to the ulcers and maintains the pH of the gastric microenvironment at ideal values for pepsin activity inhibition.

Due to sucralfate basicity, 1 g of product can neutralize approx. 13 mEq hydrogen ions.

On addition to 0.1N hydrochloric acid, sucralfate in powder form rapidly becomes tacky and adhesive, and yields approx. 10% of its antacid power within 2 to 3 minutes. After said initial yield, even if the reaction medium is maintained under vigorous stirring, the reaction with the acid becomes very slow as it is hindered by the paste viscosity.

Therefore, although sucralfate is suitable for the treatment of ulcers, it cannot be used as an antiacid.

In fact, as well known to those skilled in the art, the therapeutic activity of antacid preparation depends not only on its absolute acidity neutralization, but also and especially on its acidity neutralization rate in the gastric environment.

Advanced pharmacopoeias state that the therapeutic activity of an antacid preparation is a function of two basic parameters: reaction rate and neutralization duration.

The first parameter, i.e. the reaction rate, concerns acidity neutralization for a fast relief of the heartburn sensation (pyrosis) generally accompanying gastric hyperacidity; the second parameter, i.e. neutralization duration, concerns the development of a buffer action maintaining for an appropriate time the gastric lumen pH above the value at which said painful sensation is no more felt.

As concerns the first parameter, sucralfate exerts a poor action: paste formation considerably slows down its reactivity and, therefore, a pH value compatible with pyrosis suppression cannot be obtained. As concerns the second parameter, sucralfate is unable to maintain the pH value reached for an appropriate time: theoretically it can maintain the gastric environment buffered, but in fact, against a continuous secretion of the gastric juice, it does not exert any buffering action due to the low reactivity of the paste that formed.

It follows that sucralfate can exert an antacid action only if chemically transformed into a specific antiacid product, as disclosed in EP 437406. Therefore, sucralfate powder cannot constitute an efficacious active ingredient of an antacid, preparation.

EP 286978 by the Applicant discloses sucralfate in the form of gel, with particles dimensional distribution practically at the limit of colloidal size, which secures a very high specific surface of the product.

Sucralfate gel exerts a more potent antiulcer action than the powder form of general use and, when contacted with acids, does not form the paste already mentioned. The higher activity of the product was proved to result from its specific ability to adhere to the mucosa, i.e. from the bioadhesion, taking place without any intervention of the acids.

The sucralfate gel aqueous suspension shows unique thixotropic-type theological properties revealing a considerable surface activity of the particles, which very easily gives rise to interactions both with one another and with the biological substrates.

SUMMARY OF THE INVENTION

Figure 1:
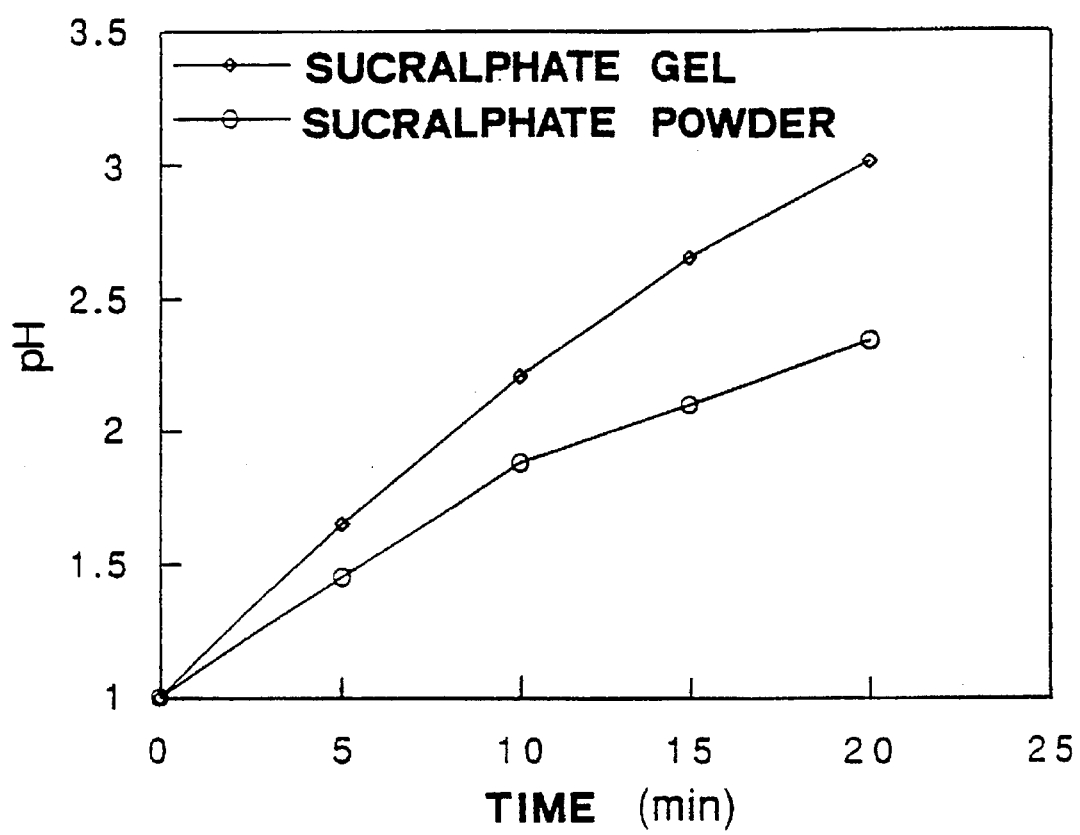
FIG. 1 illustrates the change of pH on addition of 0.5N HCl to 1 g of sucralfate gel and, respectively, sucralfate powder at 25° C.
Figure 2:
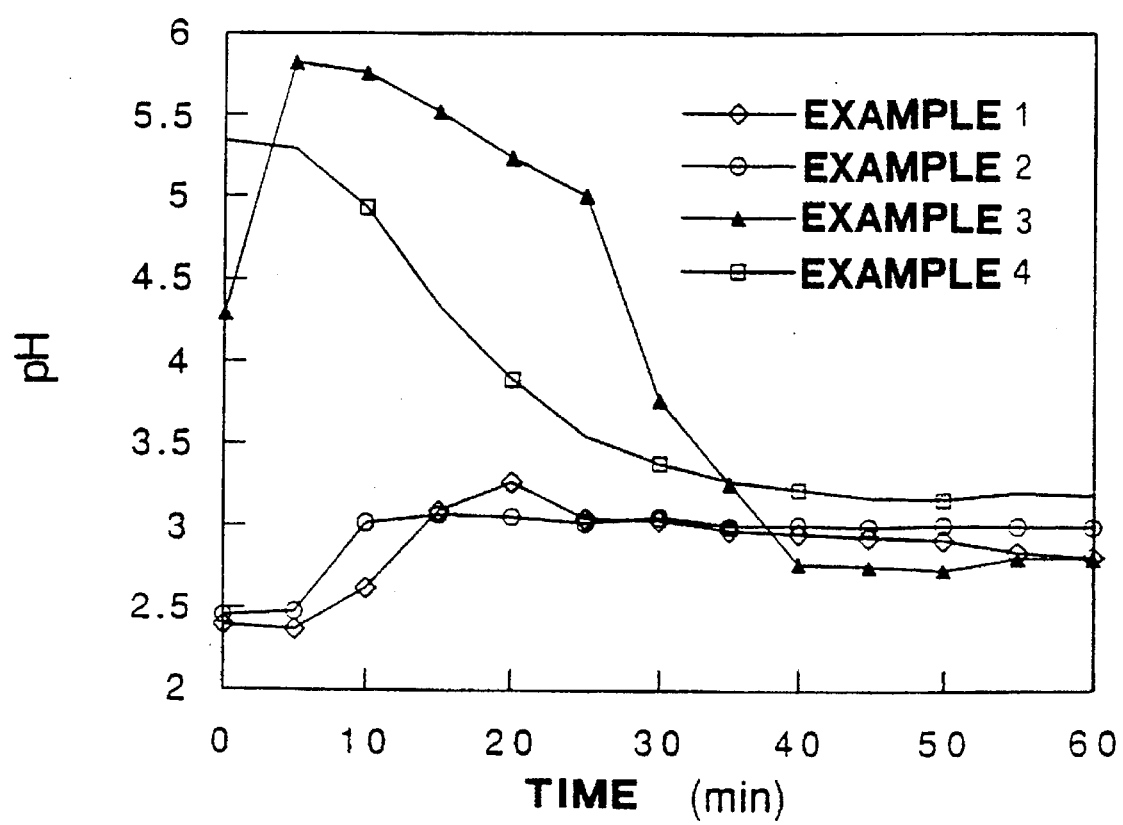
FIG. 2 shows the antacid, effectiveness by Rosset-Rice's test and the results obtained with antacid doses as per Examples 1, 2, 3, and 4.
Figure 3:
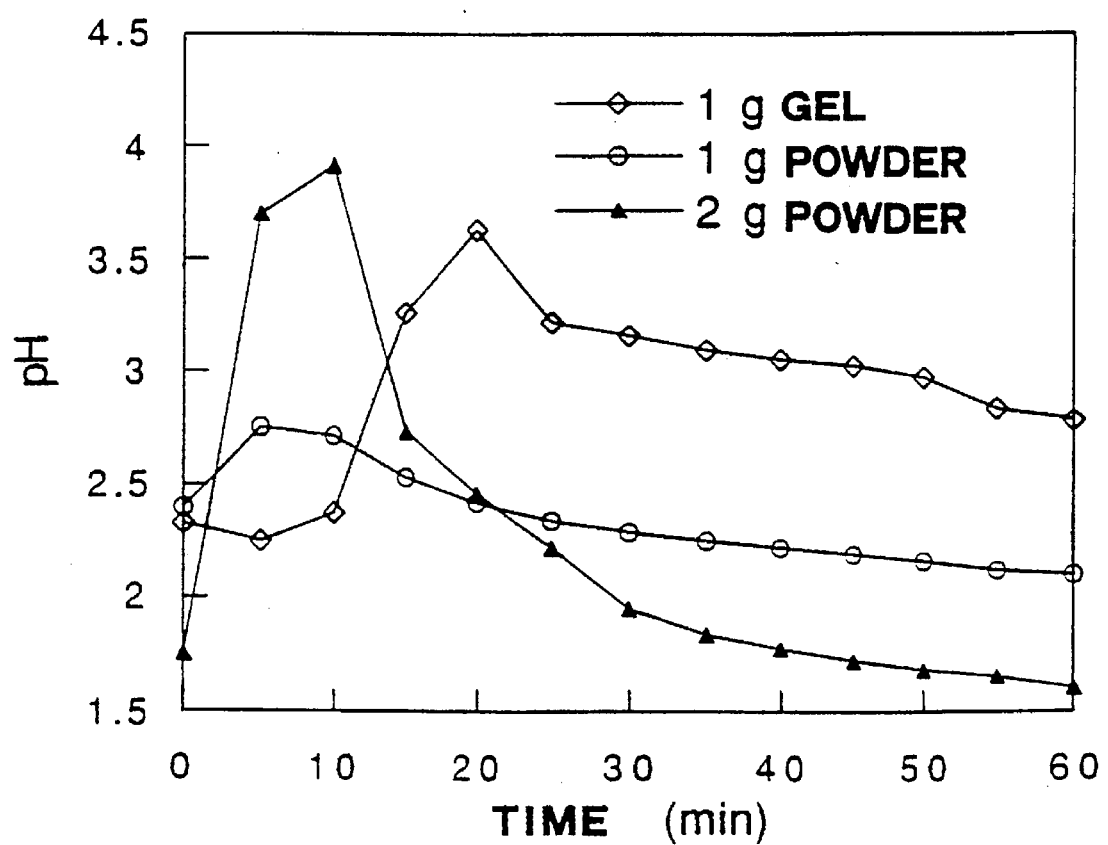
FIG. 3 shows the antacid effectiveness by Rosset-Rice's test and the results obtained by testing doses of 1 g sucralfate powder, 1 g of sucralfate gel, and 2 g of sucralfate powder.

It has surprisingly been found that sucralfate gel shows a rate of reaction with the acids and acidity neutralization power decidedly superior to sucralfate in the powder form, as elucidated in FIG. 1. This figure illustrates the change of pH on addition of 0.5N HCl to 1 g of sucralfate gel and, respectively, sucralfate powder at 25° C.

It is an object of the present invention to provide antacid pharmaceutical compositions in the form of suspensions containing sucralfate gel as an active ingredient, combined with suitable excipients and/or diluents, particularly suitable for the treatment of pyrosis and gastroesophageal backflow.

DETAILED DESCRIPTION OF THE INVENTION

According to US Pharmacopoeia USP XXII, an antacid preparation is generally considered safe and effective when it obeys the safety and effectiveness requirements ("Antiacid Effectiveness" requirements). To meet said requirements, the product has to pass a preliminary test meant to establish whether it may be defined antacid or not. Said test consists in causing a single minimum dose of substance supposed to be antiacid to react with 0.5N hydrochloric acid for 10 minutes. Should the substance being tested under such conditions be capable of bringing the solution pH to values above 3.5, the preparation will be considered antiacid.

Should said preliminary test give positive results, a second test will be conducted to determine the acidity neutralization power of the substance. Said power must be such that the aforesaid single minimum dose of the substance supposed to be antiacid can neutralize at least 5 mEq of acid.

It has surprisingly been found by the Applicant that sucralfate gel at 37° C. shows an acidity neutralization rate allowing it to pass the USP XXII preliminary test.

In particular, in the preliminary antacid effectiveness test as per USP XXII, already a dose of 1.5 g brings pH to values exceeding 3.5. In the second antacid test which is meant to determine the neutralization power, the said dose was found to neutralize 23 mEq against the limit value of 20 to 25 mEq set by USP XXII.

Vice versa, in the preliminary test, the same dose of product containing commercially available sucralfate powder gives pH values ranging from 1.2 to 1.6. Evidence is thus provided that sucralphate powder is unable to exert an antiacid action.

The sucralfate gel content in the suspension preferably ranges from 10 to 20%, w/v.

In particular, the therapeutic compositions of the present invention contain 1.5 to 4 g sucralfate per dosage unit and, preferably, 2 g sucralfate per dosage unit.

Furthermore in water dispersion sucralfate gel is self-suspending: in other words, no other suspending agent is needed to obtain stable suspensions. Therefore, sucralfate gel can be used as a suspending agent to prepare antiacid suspensions in which other antiacids are stably suspended.

The use of sucralfate gel as a suspending agent allows obtaining a safe and effective sucralfate-based antiacid preparation matching two important goals. First, the antiacid action of sucralfate gel may be strengthened by the addition of a dose of another antiacid with the result that a more potent anti-acid action is obtained. Second, the use of sucralfate in conjunction with another antiacid active ingredient, such as for example magnesium hydroxide or salts thereof, brings a therapeutic benefit: i.e. the astringent effect on the intestine function typical of sucralfate is limited by the laxative effect typical of magnesium salts.

It follows that the claimed compositions may also contain another conventional antiacid, if any, said antiacid being preferably selected among magnesium hydroxide, magnesium carbonate and calcium carbonate.

In this case, 1 g of sucralfate was found to be sufficient for an optimal antacid-suspending effect.

The preferred dose of sucralfate, when combined with another antiacid active ingredient preferably ranges from 1 to 3 g and the dose of said antiacid active ingredient ranges from 0.250 to 0.750 g.

The following examples of antiacid preparations obtained according to the present invention are conveyed by way of indication, not of limitation.

EXAMPLE 1

One 10 ml dose of suspension contains:

| | |
|---|---|
| Sucralfate gel (corresponding to 927 mg AL(OH)$_3$) | 1.500 g |
| Methyl-p-hydroxybenzoate sodium salt | 0.020 g |
| Propyl-p-hydroxybenzoate sodium salt | 0.010 g |
| Sorbitol 70% | 2.700 g |
| Apple flavouring | 0.014 g |
| Purified water | q.s. | p-Hydroxybenzoates were dispersed in liquid sorbitol and wet sucralfate gel was added. The resulting mixture was dispersed to give a thick and fluid cream, which was added with the flavouring agent, made up to volume with water, turbine-stirred without embodiment, to yield a fluid and translucent suspension.

EXAMPLE 2

One 15 ml dose of suspension contains:

| | |
|---|---|
| Sucralfate gel (corresponding to 1,324 mg AL(OH)$_3$) | 2.000 g |
| Methyl-p-hydroxybenzoate sodium salt | 0.030 g |
| Propyl-p-hydroxybenzoate sodium salt | 0.015 g |
| Sorbitol 70% | 4.600 g |
| Apple flavouring | 0.014 g |
| Purified water | q.s. |

This suspension was prepared according to Example 1.

EXAMPLE 3

One 7.5 ml dose of suspension contains:

| | |
|---|---|
| Sucralfate gel (corresponding to 662 mg AL(OH)$_3$) | 1.000 g |
| Magnesium hydroxide | 0.281 g |
| Methyl-p-hydroxybenzoate sodium salt | 0.016 g |
| Propyl-p-hydroxybenzoate sodium salt | 0.008 g |
| Sorbitol 70% | 2.300 g |
| Apple flavouring | 0.014 g |
| Purified water | q.s. |

This suspension was prepared according to Example 1.

EXAMPLE 4

One 7.5 ml dose of suspension contains:

| | |
|---|---|
| Sucralfate gel (corresponding to 662 mg Al(OH)$_3$) | 1.000 g |
| Magnesium carbonate | 0.400 g |
| Methyl-p-hydroxybenzoate sodium salt | 0.016 g |
| Propyl-p-hydroxybenzoate sodium salt | 0.080 g |
| Sorbitol 70% | 2.300 g |
| Apple flavouring | 0.014 g |
| Purified water | q.s. |

This suspension was prepared according to Example 1.

The test as per USP XXII conducted on the formulation of Example 1 for the determination of the antiacid effectiveness gave the following results:

preliminary antacid power (pH>3.5): pH 3.65
neutralization power (>20.25 mEq): 23 mEq.

The test as per USP XXII conducted on the formulation of Example 2 for the determination of the antiacid effectiveness gave the following results:

preliminary antacid power (pH>3.5): pH 3.85
neutralization power (>28.93 mEq): 27 mEq.

The test as per USP XXII conducted on the formulation of Example 3 for the determination of the antiacid effectiveness gave the following results:

preliminary antacid power (pH>3–5): pH 5.6
neutralization power (>21.73 mEq): 27.0 mEq.

The test as per USP XXII conducted on the formulation of Example 4 for the determination of the antiacid effectiveness gave the following results:

preliminary antacid power (pH>3.5): pH 5.6
neutralization power (>21.8 mEq): >28.3 mEq.

ROSSET-RICE DYNAMIC TEST

Rosset-Rice's dynamic test (N. E. Rosset and M. L. Rice, Gastroenterology, 26, 940, 1954) was also conducted on the preparations of the present invention further to prove the effectiveness of the antiacid dose of same. According to this test, a 400 ml beaker containing water (70 ml) and 0.1N HCl (30 ml) maintained at 37° C. was fed with a dose of antacid. After addition of 2 ml/min of 10N HCl the change in pH was measured under continuous magnetic stirring (300 rpm/min).

The antacid, dose is considered effective when a pH value of 3.0 is reached within 10 minutes and maintained above said value for over one hour.

With reference to the figures the Rosset-Rice's test provided evidence that all products possessed antacid effectiveness. sucralfate gel at a dose of 1 g shows some antacid power and sucralfate powder at a dose of 2 g reaches a pH value of 3 within 10 minutes, but cannot maintain said value for over 15 minutes, during which 2 ml/min HCl was added to simulate gastric secretion.

I claim:

1. A therapeutic method for the treatment of gastric hyperacidity comprising orally administering to a patient in need of such a treatment an antacid effective amount of sucralfate gel.

2. The therapeutic method according to claim 1, wherein said sucralfate gel is administered in the form of aqueous suspensions containing sucralfate gel in amounts ranging from 1.5 to 20% w/v.

3. The therapeutic method according to claim 1, wherein another antacid ingredient is optionally administered with sucralfate gel.

4. The therapeutic method according to claim 3, wherein said antacid is selected from the group consisting of magnesium hydroxide, magnesium carbonate, and calcium carbonate.

* * * * *